United States Patent
Aebischer et al.

(10) Patent No.: US 10,835,621 B2
(45) Date of Patent: Nov. 17, 2020

(54) BICISTRONIC AAV VECTOR FOR RNA INTERFERENCE IN ALS

(71) Applicant: Ecole Polytechnique Federale De Lausanne (EPFL), Lausanne (CH)

(72) Inventors: Julianne Aebischer, Lausanne (CH); Bernard Schneider, Lausanne (CH); Cylia Rochat, Lausanne (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 75 days.

(21) Appl. No.: 15/746,458

(22) PCT Filed: Jul. 22, 2016

(86) PCT No.: PCT/EP2016/067549
§ 371 (c)(1),
(2) Date: Jan. 22, 2018

(87) PCT Pub. No.: WO2017/013252
PCT Pub. Date: Jan. 26, 2017

(65) Prior Publication Data
US 2018/0228919 A1   Aug. 16, 2018

(30) Foreign Application Priority Data

Jul. 22, 2015 (EP) .................................... 15177828

(51) Int. Cl.
*A61K 48/00* (2006.01)
*C12N 15/86* (2006.01)
*C12N 15/113* (2010.01)
*C12N 15/79* (2006.01)

(52) U.S. Cl.
CPC ........ *A61K 48/0058* (2013.01); *C12N 15/113* (2013.01); *C12N 15/79* (2013.01); *C12N 15/86* (2013.01); *C12N 2750/14141* (2013.01); *C12N 2750/14143* (2013.01); *C12N 2830/008* (2013.01); *C12N 2830/20* (2013.01); *C12N 2830/42* (2013.01); *C12N 2830/48* (2013.01); *C12N 2830/50* (2013.01)

(58) Field of Classification Search
CPC .... A61K 48/0058; C12N 15/13; C12N 15/79; C12N 15/86; C12N 2830/008; C12N 2830/20
USPC .............. 435/6.1, 91.1, 91.31, 455, 458; 514/44 A; 536/23.1, 24.5
See application file for complete search history.

(56) References Cited

FOREIGN PATENT DOCUMENTS

WO   2015031392 A1   3/2015

OTHER PUBLICATIONS

PCT International Preliminary Report on Patentability, Application No. PCT/EP2016/067549 dated Jan. 23, 2018.
Foust et al., "Therapeutic AAV9-mediated Suppression of Mutant SOD1 Slows Disease Progression and Extends Survival in Models of Inherited ALS", Dec. 2013, Molecular Therapy, vol. 21, No. 12, pp. 2148-2159.
Bobela-Aebischer et al., "Use of a Bicistronic Vector to Silence SOD1 in Motoneurons and Astrocytes for the Treatment of Familial Amyotrophic Lateral Sclerosis", May 2016, Molecular Therapy, vol. 24, Supplement 1.
Dirren et al., "SOD1 silencing in motoneurons or glia rescues neuromuscular function in ALS mice", 2015, Annals of Clinical and Translational Neurology, vol. 2, No. 2, pp. 167-184.

*Primary Examiner* — Jane J Zara
(74) *Attorney, Agent, or Firm* — MacMillan, Sobanski & Todd, LLC

(57) ABSTRACT

The present invention relates to a bicistronic expression vector for silencing a gene specifically in astrocytes and neurons, comprising two expression cassettes comprising a first and a second silencer sequence, respectively, wherein the expression of said first silencer sequence within astrocytes is regulated by an astrocyte-specific promoter and the expression of said second silencer sequence within neurons is regulated by a neuron-specific promoter. In a preferred embodiment, said first and second silencer sequences are SOD1 silencer sequences. Pharmaceutical composition comprising said bicistronic vector and the use of the same in the treatment of motoneuron diseases are further described.

16 Claims, 6 Drawing Sheets

Specification includes a Sequence Listing.

SEQUENCE LISTING

<160> NUMBER OF SEQ ID NOS: 2

<210> SEQ ID NO 1

```
<211> LENGTH: 21
<212> TYPE: DNA
<213> ORGANISM: Homo sapiens

<400> SEQUENCE: 1
attactttcc ttctgctcga a                                              21

<210> SEQ ID NO 2
<211> LENGTH: 134
<212> TYPE: DNA
<213> ORGANISM: Artificial Sequence
<220> FEATURE:
<223> OTHER INFORMATION: miRNA + flanking regions

<400> SEQUENCE: 2
ccuggaggcu ugcugaaggc uguaugcuga uuacuuuccu ucugcucgaa gttuuggcca    60
cugacugacu ucgagcaagg aaaguaauca ggacacaagg ccuguuacua gcacucacau   120
ggaacaaaug gccc                                                    134
```

BICISTRONIC AAV VECTOR FOR RNA INTERFERENCE IN ALS

This is a national stage application filed under 35 U.S.C. § 371 of international application PCT/EP2016/067549, filed under the authority of the Patent Cooperation Treaty on Jul. 22, 2016, published; which claims the benefit of EP Application No. 15177828.9 filed on Jul. 22, 2015. The entire disclosures of all the aforementioned applications are expressly incorporated herein by reference for all purposes.

The present invention relates to a bicistronic expression vector for silencing a gene specifically in astrocytes and neurons, comprising two expression cassettes comprising a first and a second silencer sequence, respectively, wherein the expression of said first silencer sequence within astrocytes is regulated by an astrocyte-specific promoter and the expression of said second silencer sequence within neurons is regulated by a neuron-specific promoter. In a preferred embodiment, said first and second silencer sequences are SOD1 silencer sequences.

Pharmaceutical composition comprising said bicistronic vector and the use of the same in the treatment of motoneuron diseases are further described.

BACKGROUND

Motoneuron diseases are a group of progressive neurological disorders that destroy motoneuron, the cells that control essential voluntary muscle activity such as speaking, walking, breathing, and swallowing. Normally, messages from nerve cells in the brain (called upper motoneuron) are transmitted to nerve cells in the brain stem and spinal cord (called lower motoneuron) and from them to particular muscles. When there are disruptions in the signals between the lowest motoneuron and the muscle, the muscles do not work properly; the muscles gradually weaken and may begin wasting away and develop uncontrollable twitching. When there are disruptions in the signals between the upper motoneurons and the lower motoneuron, the limb muscles develop stiffness (called spasticity), movements become slow and effortful, and tendon reflexes such as knee and ankle jerks become overactive. Over time, the ability to control voluntary movement can be lost.

In adults, the most common motoneuron disease is amyotrophic lateral sclerosis (ALS), a fatal neurodegenerative disorder. So far, the sole approved drug, Riluzole, delays the course of the disease by only a few months.

In Europe and North America, the incidence of ALS is about 2 cases per year per 100,000, while prevalence is around 5 cases per 100,000 with approximately 7,000 cases diagnosed annually in the US. Incidence increases with age, especially after 40, to reach a peak in the mid 70's. While age is a leading risk factor, genetics is also important, with about 1 in 10 cases of ALS being familial (FALS). Mutations in the superoxide dismutase 1 (SOD1) gene account for 20% of familial forms of the disease. Genetic analyses of sporadic ALS cases (SALS) have demonstrated significant associations between SALS and a range of loci. Mutations in loci more typically associated with FALS (SOD1 and others) have also been detected in SALS cases.

Several mouse and rat models expressing mutant forms of SOD1 exist. Transgenic mouse models expressing the human SOD1 gene harboring a G93A, G37R, or G85R mutation develop a phenotype similar to what is observed in human ALS patients; the transgenic SOD1 mouse is considered the most accurate representation of the disease process.

Mutant SOD1 exerts multiple pathogenic effects through the gain of toxic properties in both neurons and glial cells. Indeed, in vitro experiments, based on motoneuron-glia co-culture systems, as well as investigations performed in mutant SOD1 mice have revealed non-cell autonomous disease processes (Lasiene and Yamanaka, 2011). While the expression of mutant SOD1 in motoneurons mainly determines disease onset, SOD1 pathology in non-neuronal cell types plays a key role in disease progression. In particular, removal of mutant SOD1 in astrocytes, or spinal cord enrichment in wild-type (WT) astrocytes, prolongs the survival of mutant SOD1 animals by slowing down late-stage disease progression (Lepore, Rauck et al., 2008; Yamanaka, Chun et al., 2008; Boucherie, Schafer et al., 2009; Wang, Gutmann et al., 2011). Further supporting the gain of toxic activities by mutated SOD1, SOD1 null mice do not show signs of motoneuron degeneration (Reaume, Elliott et al., 1996; Ho, Gargano et al., 1998).

Adeno-associated viruses (AAV) are promising vectors for in vivo gene delivery. A number of naturally occurring serotypes and subtypes have been isolated from human and non-human primate tissues; some of them are of interest, given their capability to transduce various organs including central nervous system with high efficiency.

Recently, a major therapeutic breakthrough has been achieved using a single intravenous injection of AAV of serotype 9 (AAV9) encoding small hairpin RNA (shRNA) against human SOD1 (Foust, Salazar et al., 2013). When administrated at birth, AAV9 infects approximately 60% of motoneurons and 30% of astrocytes which, in the case of shRNA targeting SOD1 mRNA, translates into delayed disease onset, improved motor performances and around 40% extension in the survival of treated mice. When injected into adult mice, AAV9 combined with the cba promoter leads to a pattern of transgene expression that is higher in astrocytes (around 50%) than in motoneurons (8%). It is however possible that the expression of the shRNA, which is in the same vector but under control of the H1 pol-III promoter, has a different pattern in these animals. Interestingly AAV9-shRNA remains therapeutic when delivered after disease onset and prolongs the survival of SOD1 mice, albeit to a lesser extent than early treatments.

A second study used recombinant AAV rhesus-10 (rAAVrh10) to deliver artificial micro RNA (miRNA) designed to suppress SOD1 (miR SOD1) expression. The miR SOD1 transcription was under the control of the constitutively active cba promoter. Following intrathecal administration to adult ALS mice, this vector led to a predominance of transgene expression in astrocytes, which slowed down disease progression (Wang, Yang et al., 2014).

In the study of Dirren, Aebischer et al., 2015 two separate vectors have been used to target either astrocytes or motoneurons. The two vector systems were designed to suppress SOD1 expression predominantly in spinal motoneurons using the AAV6 capsid in combination with the constitutively active cmv promoter, or in astrocytes, using AAV9 with the astrocyte-specific gfaABC₁D promoter. In adult mice, AAV9 serotype with the cmv-driven cassette has been used, as AAV9 appeared to be more efficient than AAV6 to target motoneurons.

Following vector administration to both newborn and adult ALS mice, most complete protection of motor units was obtained when targeting human SOD1 principally in motoneurons. Remarkably, suppressing SOD1 in astrocytes also showed neuroprotective effects, which were clearly different from those observed with the motoneuron-targeting vector. Although only partial protection of spinal motoneurons has been observed when suppressing SOD1 in astrocytes, muscle innervation was nearly completely preserved, indicating a possible effect on the ability of the remaining motoneurons to re-innervate the muscle. Indeed, the recovery of the neuromuscular function was similar to the condition where SOD1 was silenced in motoneurons. With each of these vectors, gene therapy significantly prolonged survival of ALS mice when administered to newborn mice. Therefore, while SOD1 silencing in motoneurons is most effective at protecting these cells in the ALS mouse model, targeting SOD1 in astrocytes is required to restore neuromuscular function. However, a major drawback of the tested approach has to be found in the use of two vectors to address two different cellular types. The combined injection of two viral vectors entails several problems, among these:

i) the viral load i.e. obtaining the optimum viral load for two vectors as to obtain therapeutic efficacy, hits the limit of physical property, concerning the maximal dose tolerated by the organism;

ii) the volume restrictions relating to injection and delivery methods.

The above-indicated problems cannot be overcome simply by multiple, independent injections, given that it is known that multiple injections increase the risk for an immune system reaction.

There is a strong need for an approach suitable for a clinical setting and capable to address mutant SOD1 both in motoneurons and astrocytes in order to achieve therapeutic efficacy in motoneuron diseases.

SUMMARY OF THE INVENTION

The present invention relates to a bicistronic expression vector for silencing a gene specifically in astrocytes and neurons, comprising two expression cassettes comprising a first silencer sequence and a second silencer sequence, respectively, wherein the expression of said first silencer sequence within astrocytes is regulated by an astrocyte-specific promoter and the expression of said second silencer sequence within neurons is regulated by a neuron-specific promoter. In a preferred embodiment, said first and second silencer sequences are SOD1 silencer sequences.

Pharmaceutical composition comprising said bicistronic vector and the use of the same in the treatment of motoneuron diseases are further described.

DETAILED DESCRIPTION

Figure 1:
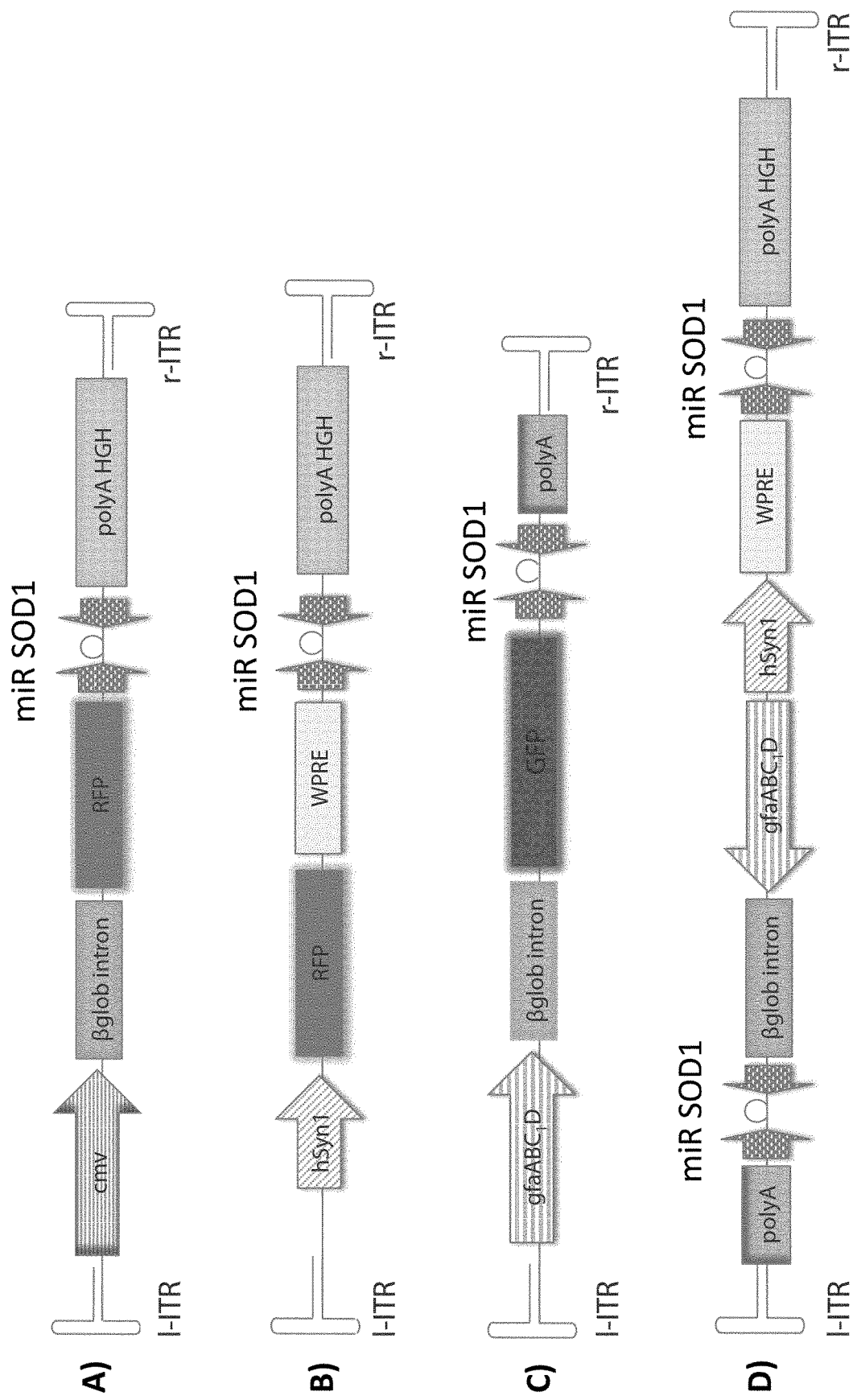
FIG. 1: cartoon diagram of vectors used in the present invention. A), B), C) comparative examples. D) an embodiment of the bicistronic vector of the present invention.

The present invention describes a bicistronic expression vector, allowing continuous expression of a first and a second silencer sequence specifically in motoneurons and astrocytes.

The bicistronic expression vector of the present invention comprises a first expression cassette comprising a first nucleotide sequence encoding a first silencer sequence operably linked to a promoter functional in astrocytes and a second expression cassette comprising a second nucleotide sequence encoding a second silencer sequence operably linked to a promoter functional in neurons.

Said bicistronic vector, in a preferred embodiment, comprises, in both said first and second cassettes, a posttranscriptional regulatory element upstream of said sequences encoding said silencer sequences and a polyA tail downstream from the same.

In a preferred embodiment, said first and second silencer sequences are SOD1 silencer sequences.

In a further preferred embodiment, said vector is an AAV vector and the regulatory sequences are selected so that the total size of the vector is below 5 kb, which is compatible with packaging within the AAV capsid. Said AAV vector is of any serotype compatible with widespread transgene delivery to astrocytes and motoneurons; preferably, said AAV vector is of serotype 9 or of serotype 6.

In a preferred embodiment, the astrocyte specific promoter is selected from the group comprising the GFAP promoter, the glutamine synthase promoter, preferably is the minimal GFAP promoter gfaABC$_1$D; the neuron specific promoter is selected from the group comprising synapsin, cmv, platelet-derived growth factor B-chain (PDGF-β), the methyl-CpG binding protein 2 (MeCP2), preferably it is the human synapsin I promoter hSyn1.

The above indicated mammalian promoters are compatible with long-term transgene expression and they are known to restrict the expression of the controlled gene to subsets of cells of interest in the CNS.

Said SOD1 silencer sequence is selected from the group comprising RNA sequences that can be transcribed from naturally occurring or artificial DNA to interfere with SOD1 expression, including small hairpin RNA (shRNA) against SOD1, micro RNA (miRNA) against SOD1, antisense RNA sequences against SOD1, or guide RNA sequences for CRISPR/Cas9 targeting of the SOD1 gene. In a preferred embodiment, the SOD1 silencer is a miRNA targeting SOD1 mRNA, preferably targeting the nt 209-229 (SEQ ID No. 1) (miR SOD1) of the coding sequence of human SOD1. For the purpose of the present invention, miR SOD1 is related to a miRNA targeting SOD1, where said SOD1 targeting sequence is referred to the nt 209-229 of the coding sequence of human SOD1 (SEQ ID No. 1).

In a further preferred embodiment, said miRNA sequence comprises a 6 or 7 nucleotides-long "seed" sequence which is fully homologous to the human SOD1 mRNA transcript (NM_000454).

In a further preferred embodiment miRNA mature sequence has at least 50%, 60%, 80%, 90% sequence homology, wherein for the scope of the present invention sequence homology is referred to sequence identity, with the corresponding coding sequence set forth in SEQ ID No. 1: 5'-ATT ACT TTC CTT CTG CTC GAA-3' (SEQ ID. No. 1). More preferably, said miRNA mature sequence corresponds to the coding sequence: 5'-ATT ACT TTC CTT CTG CTC GAA-3' (SEQ ID No. 1).

In a preferred embodiment, said mature miRNA is carried by the pre-miRNA backbone of murine miR-155. The corresponding DNA sequence was synthesized and subcloned into a pAAV shuttle plasmid according to standard procedures.

The inclusion of posttranscriptional regulatory element in the expression cassette, said regulatory element being, as an example, an intron or a Woodchuck hepatitis Posttrascriptional Regulatory Element (WPRE), results in a significantly increased expression of the SOD1 silencer sequence encoded by the said vector. Said intron is preferably selected from the group comprising MVM (minute virus of mice), F.IX truncated intron 1 (human factor IX), β-globin splice donor SD/immunoglobin heavy chain splice acceptor SA, adenovirus SD/immunoglobin SA. However, other natural or artificial introns known to the person skilled in the art can be used. Alternatively, a posttranscriptional enhancer element such as the WPRE can be used.

Compared to other SOD1 silencing systems used so far in the field of ALS, this bicistronic expression vector surprisingly compiles the following advantages that are relevant to therapeutic application:
  the use of cell-type specific promoters helps limiting expression of the SOD1 silencer sequence to neurons and astrocytes. This minimizes chances of deleterious effects due to off-target silencing of SOD1 or activation of the miRNA pathways in other non-therapeutically relevant cell types. This is particularly true given that SOD1 is a ubiquitous enzyme. Only one allele is mutated in familial ALS. It is unclear whether SOD1 activity produced by the normal allele is critical to the function and survival of certain cell types. Therefore, it is preferred to limit SOD1 silencing to diseased cells, such as motoneurons and astrocytes, in order to limit the risk of unwanted side effects.
  the here obtained successful incorporation of two expression cassettes into a single vector allows to express SOD1 silencer sequence simultaneously and specifically in motoneurons and astrocytes following a single injection of a viral vector that has a tropism for the two cell types, thus avoiding the limitations of using vector cocktails. These limitations include decrease in transduction efficiency due to the lower injectable dose of each individual vector, as well as the need to develop two separate therapeutic products to be ultimately combined. Also in regulatory terms, this solution brings a considerable advantage: in the event that two separate vectors are used, two procedures are required to get the regulatory approval for both of them. In this case, the burden of a single procedure has to be afforded.

Compared to vectors with single expression cassettes, the here claimed bicistronic expression vector drastically improves the therapeutic benefits obtained by gene therapy aiming at silencing SOD1 in ALS patients.

The here claimed bicistronic expression vector allows to target two different cell types by administration of a single vector, where the combined injection of two viral vectors would not only be a problem concerning the maximal vector dose tolerated by the organism but would also significantly raise the regulatory hurdles towards clinical application.

Moreover, as it will become evident from the examples that follow, a maximization of the therapeutic efficiency is obtained. Since motoneurons and astrocytes play distinctive roles in the pathology and SOD1 silencing in each of these cell types has complementary effects, targeting both motoneurons and astrocytes is a critical factor.

It is also claimed a bicistronic expression vector according to the present invention for use in the treatment of ALS.

It is further described a pharmaceutical composition, comprising a bicistronic AAV vector comprising two expression cassettes each comprising a first and a second silencer sequence, wherein the expression of said first silencer sequence within astrocytes is regulated by an astrocyte-specific promoter and the expression of said second silencer sequence within neurons is regulated by a neuron-specific promoter and a pharmaceutically acceptable carrier for use in the treatment of motoneuron disease, preferably of ALS.

In a preferred embodiment, in said pharmaceutical composition said first and second silencer sequences are SOD1 silencer sequences.

It is further described a method of treatment of a subject in need thereof, said method comprising administering to a subject in need thereof the described vector in a range comprised between 1E12-5E14 Vector Genomes VG/kg body weight.

Said administration, in a preferred embodiment, is via the cerebrospinal fluid. More preferably, it is Intrathecal (IT), Intracisternal (IC) or Intraventricular (ICV). In a further preferred embodiment, said administration is Intravenous (IV). The recombinant virions are preferably introduced to the subject in combination with an adjunctive pharmacological therapy.

Example 1

SOD1$^{G93A}$ ALS mice, carrying a transgene which is the mutant human SOD1 containing the Gly$^{93}$-->Ala (G93A) substitution, are used in the experimental setting. SOD1$^{G93A}$ ALS mice are widely used as a model for ALS and their limbs become progressively paralyzed beginning around six to seven months of age. Life expectancy is normally four to six weeks beyond onset of symptoms. SOD1$^{G93A}$ ALS mice have a highly predictable course of denervation that takes place in two successive episodes. There is an initial pruning of fast-twitch fatigable (FF) motoneurons, resulting in the denervation of type IIb muscle fibers. Vacant neuromuscular junctions (NMJ) are then partially re-innervated by the sprouting of fast-twitch fatigue-resistant (FR) and slow-twitch fatigue-resistant (S) motoneurons until FR motoneurons also start pruning their intramuscular nerve branches leading to a sustained loss of NMJ (Pun, Santos et al., 2006; Kanning, Kaplan et al., 2010). SOD1$^{G93A}$ ALS mice were injected intrathecally at the age of 4.5 weeks with 2.1E+12 VG of either one of the following AAV9 viral vectors:
  A) AAV9-cmv-RFP-miR SOD1 (control, to silence SOD1 in motoneurons)
  B) AAV9-hsyn1-RFP-miR SOD1 (control, to silence SOD1 in motoneurons)
  C) AAV9-gfaABC$_1$D-GFP-miR SOD1 (control, to silence SOD1 in astrocytes)

D) AAV9-bicistronic miR SOD1 (vector of the present invention, to silence SOD1 in motoneurons and astrocytes).

Figure 2:
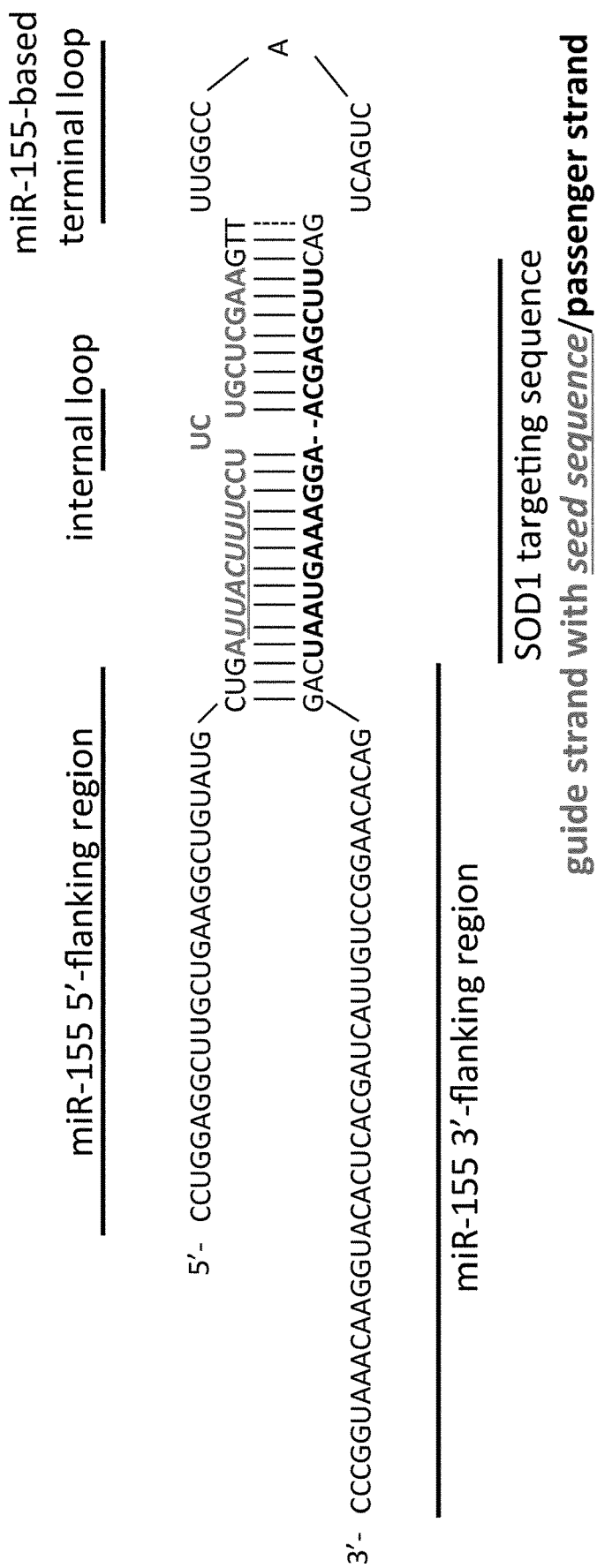
FIG. 2: SEQ ID NO.2 showing SOD1 silencer sequence (miR SOD1), miRNA stem-loops, with the guide strand shown in grey.

In FIG. 1 a schematic representation of the above-indicated vectors is reported. In this experimental setting, the SOD1 silencer sequence was engineered based on the murine miRNA-155 flanking sequences. Its guiding strand targets the nt 209-229 of the coding sequence of human SOD1 (FIG. 2). miR SOD1 is an engineered miRNA based on the flanking sequences and loop from the murine miRNA-155 sequence (represented in black in FIG. 2). It has been designed for the specific silencing of human SOD1. The SOD1 targeting sequence (bold font) is composed of a guide strand (in grey) that binds to SOD1 mRNA and contains a 7-nucleotide-long seed sequence (in italic and underlined), and the partially complementary passenger strand. Said guide strand gives rise to a miR SOD1 mature sequence, which correspond to the coding sequence SEQ ID No. 1.

To evaluate the therapeutic efficiency of these viral vectors, the four groups of mice (7 animals per group except for bicistronic vector group, which had 8 animals) were compared to PBS-injected wild-type and SOD1$^{G93A}$ ALS control animals (16 and 19 animals per group, respectively). In each group, males and females were equally distributed. Littermates were split among groups.

Electromyography (EMG) was performed on a weekly basis on the triceps surae muscles to assess neuromuscular function. EMG consists in electrically stimulating the motoneurons of the spinal cord and recording the muscular response, called Compound Muscle Action Potential (CMAP). EMG is one of the most reliable tests to predict clinical disease onset and disease progression in ALS mice (Mancuso, Osta et al., 2014) and ALS patients (Simon, Lomen-Hoerth et al., 2014).

Figure 3:
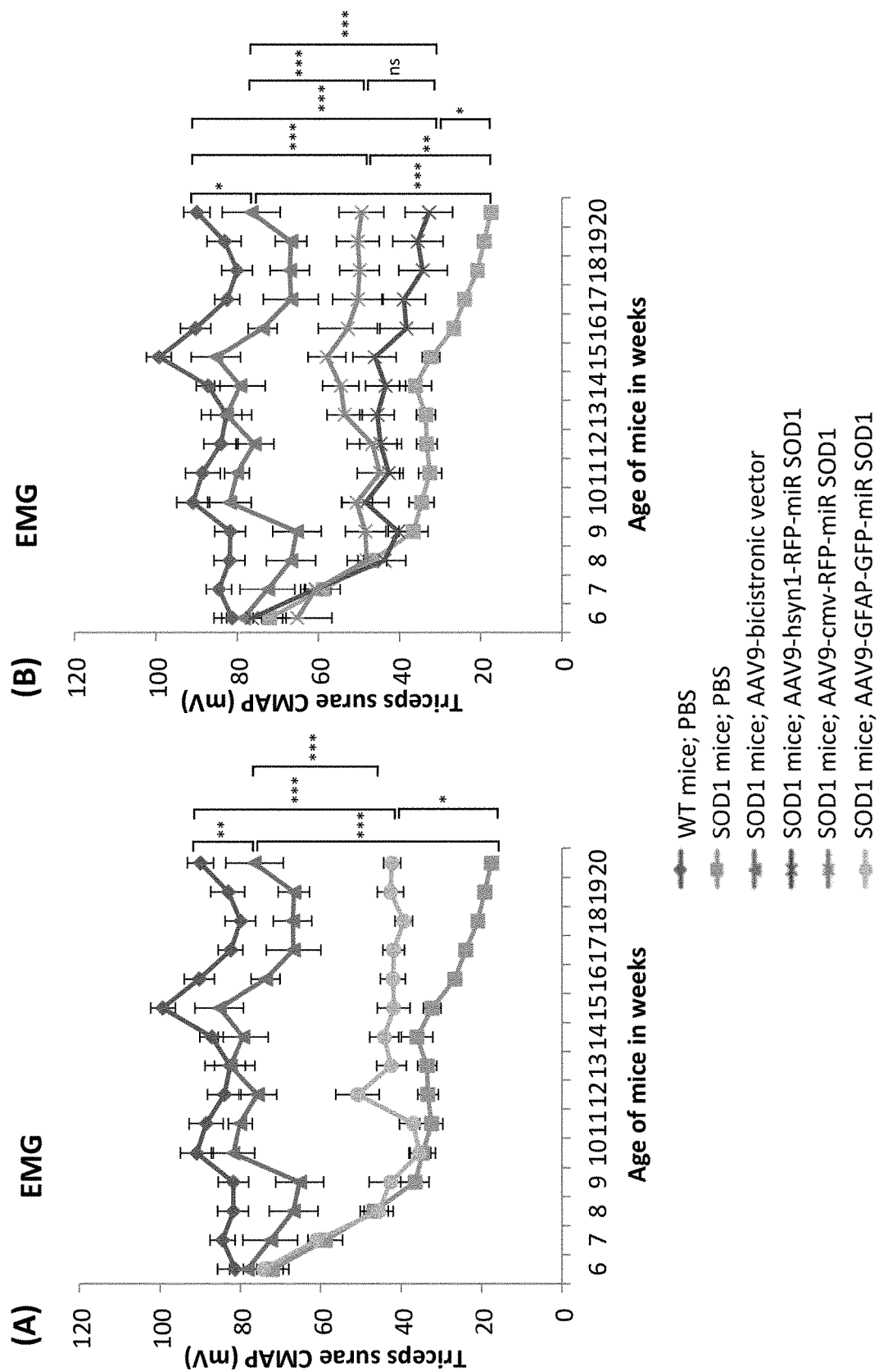
FIG. 3: compound muscle action potential measured in triceps surae muscles during time after infection of the mice. Study on the therapeutic efficiency, comparing the bicistronic vector of the present invention to an astrocyte-specific vector (GFAP promoter, panel A) and neuron-specific vectors (cmv and hsyn1 promoters, panel B).

Results are reported in the graph of FIG. 3.

In PBS-injected SOD1$^{G93A}$ mice, CMAP amplitude declined between postnatal days 50 and 60, and the amplitude then stabilized at around 40% of the starting value. At 12 weeks of age, the CMAP measurements of SOD1$^{G93A}$ control mice (33.4±10.2 mV) did not statistically differ from mice injected with AAV9 vectors silencing SOD1 in either motoneurons or astrocytes. There was, however, a trend towards improved muscle response in treated animals (AAV9-cmv-RFP-miR SOD1, 46.8±16.2 mV; AAV9-hsyn-RFP-miR SOD1, 44.7±13.4 mV; gfaABC$_1$D-GFP-miR SOD1, 50.8±14.3 mV).

Remarkably, a significant difference was already observed at 8 weeks between the AAV9-bicistronic group and control ALS mice (p<0.05). At 12 weeks of age the difference between the two groups was even more pronounced (p<0.001). Indeed, at this time point the CMAP values of animals injected with the bicistronic expression vector (75.6±13.4 mV) did not statistically differ from the values obtained for wild-type control mice (84.8±18.3 mV).

By further evaluating the CMAP at 20 weeks of age, where the symptoms are evident in the used animal model, the values obtained in the animals injected with the bicistronic expression vector are unchanged with respect to the value obtained at 12 weeks of age (76.5±7.2 mV), while the values further decreased in PBS injected SOD1 mice (17.5±1.4 mV), which is consistent with the second wave of denervation typically observed in the SOD1$^{G93A}$ mice at this age (FIG. 3). Overall, a significant difference was observed between the group injected with the bicistronic vector and the group injected with the vector containing the astrocyte-specific GFAP-promoter (p<0.001). Significant difference was as well observed between the bicistronic vector group and the groups injected with the vectors containing the promoters for preferential expression in neurons (for cmv and hsyn1, p<0.001) (FIG. 3, panel B). This surprising result confirms the validity of the here proposed approach.

Figure 4:
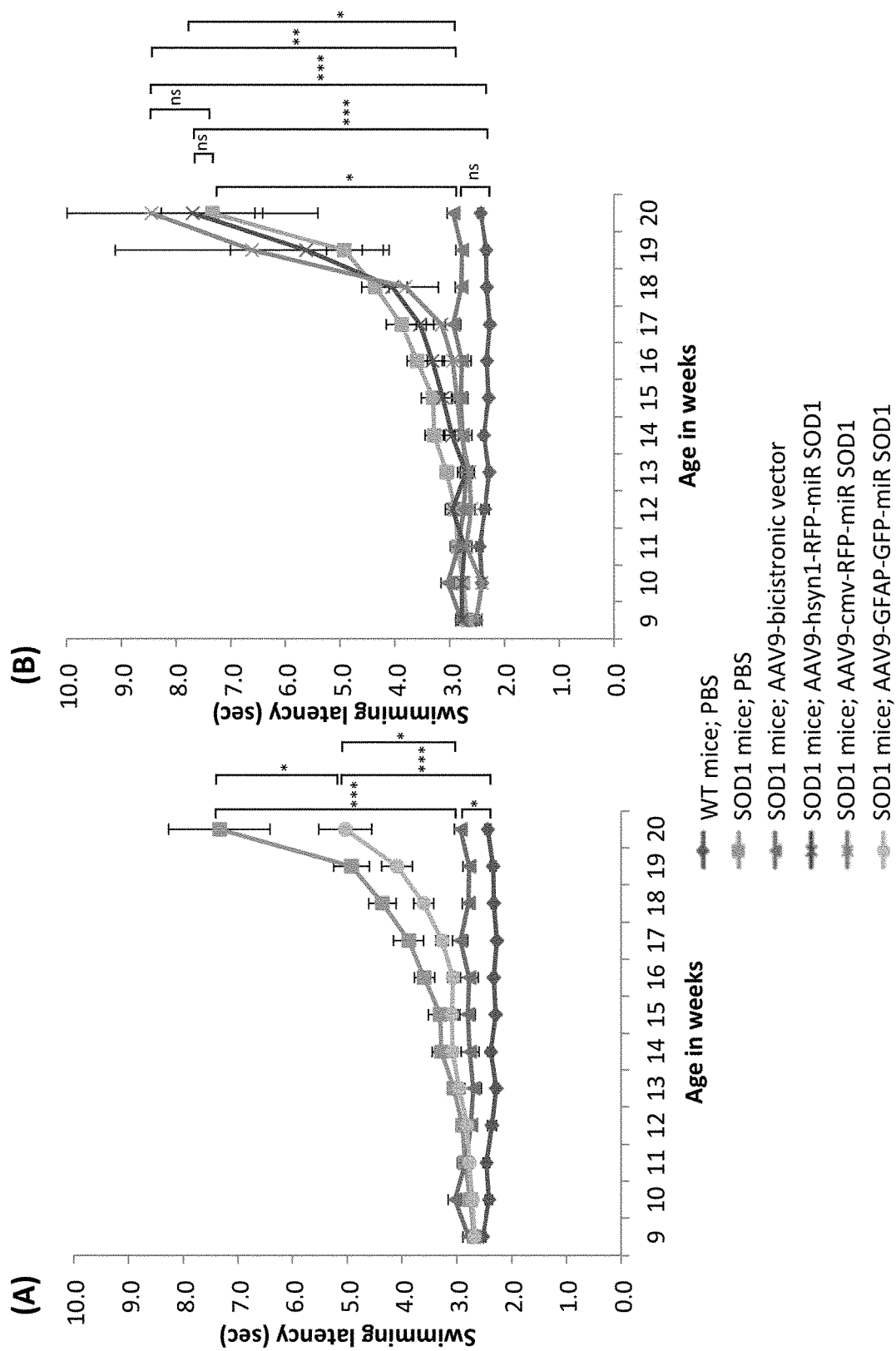
FIG. 4: the swimming performance of the mice is evaluated over time after intrathecal injection of the different vectors. Study on motor ability comparing the therapeutic efficiency of the bicistronic vector of the present invention to an astrocyte-specific vector (GFAP promoter, panel A) or neuron-specific vectors (cmv and hysn1 promoters, panel B).

This is further confirmed when assessing motor performance of the mice, by measuring the time taken by the animals to swim to a 1 m distant platform. Results are represented in FIG. 4. Overall, a significance difference in swimming performance was observed between the group injected with the bicistronic vector and the group injected with the vector containing the astrocyte-specific GFAP promoter (p<0.05). A significant difference was as well observed between the bicistronic vector group and the group injected with vectors containing the promoters for preferential expression in neurons (for cmv p<0.01 and for hysn1 p<0.05), while almost no significative difference was observed between the motor performances of the bicistronic group and the group of the wild-type control animals.

These results clearly demonstrate the superior therapeutic potential of the here claimed bicistronic expression vector when compared to expression vectors carrying a single expression cassette that expresses the miR SOD1 in motoneurons or astrocytes only.

Figure 5:
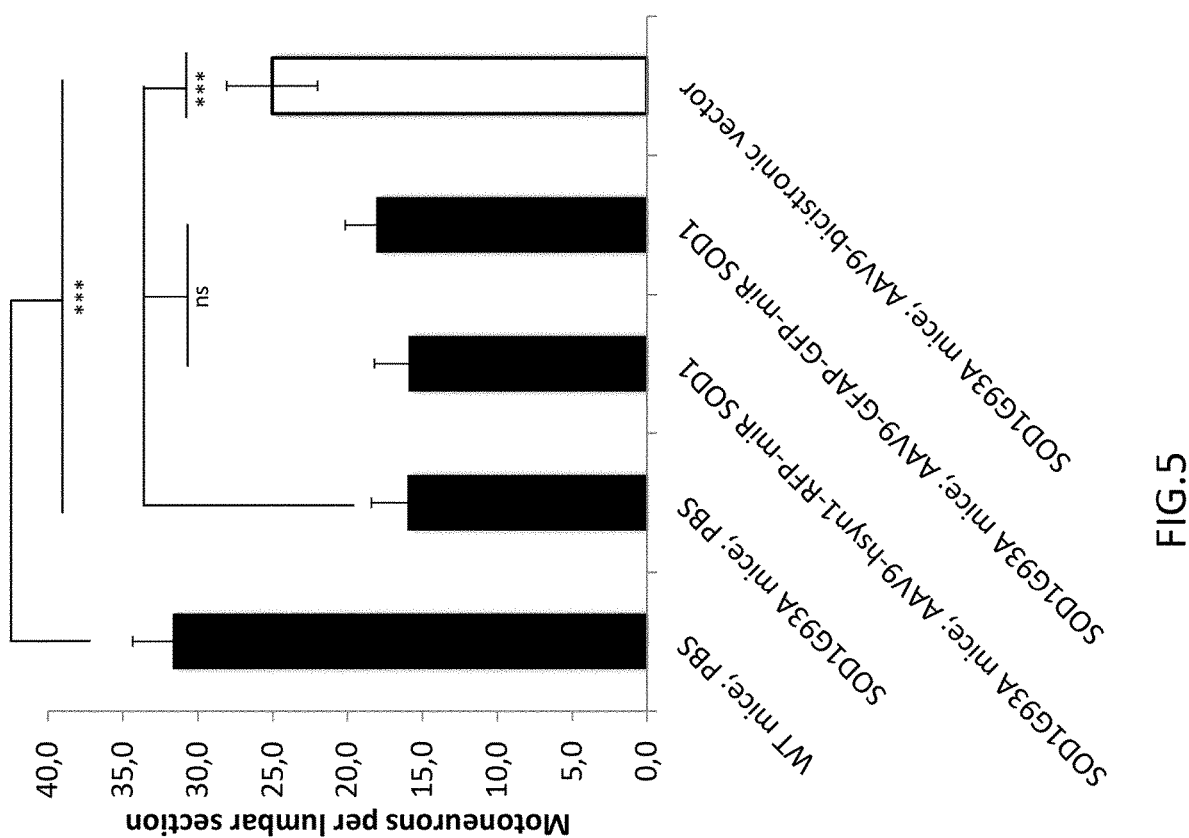
FIG. 5: Motoneuron counts per lumbar spinal cord section. Motoneuron numbers are significantly increased for the bicistronic group (white column) when compared to transgenic control animals.
Figure 6:
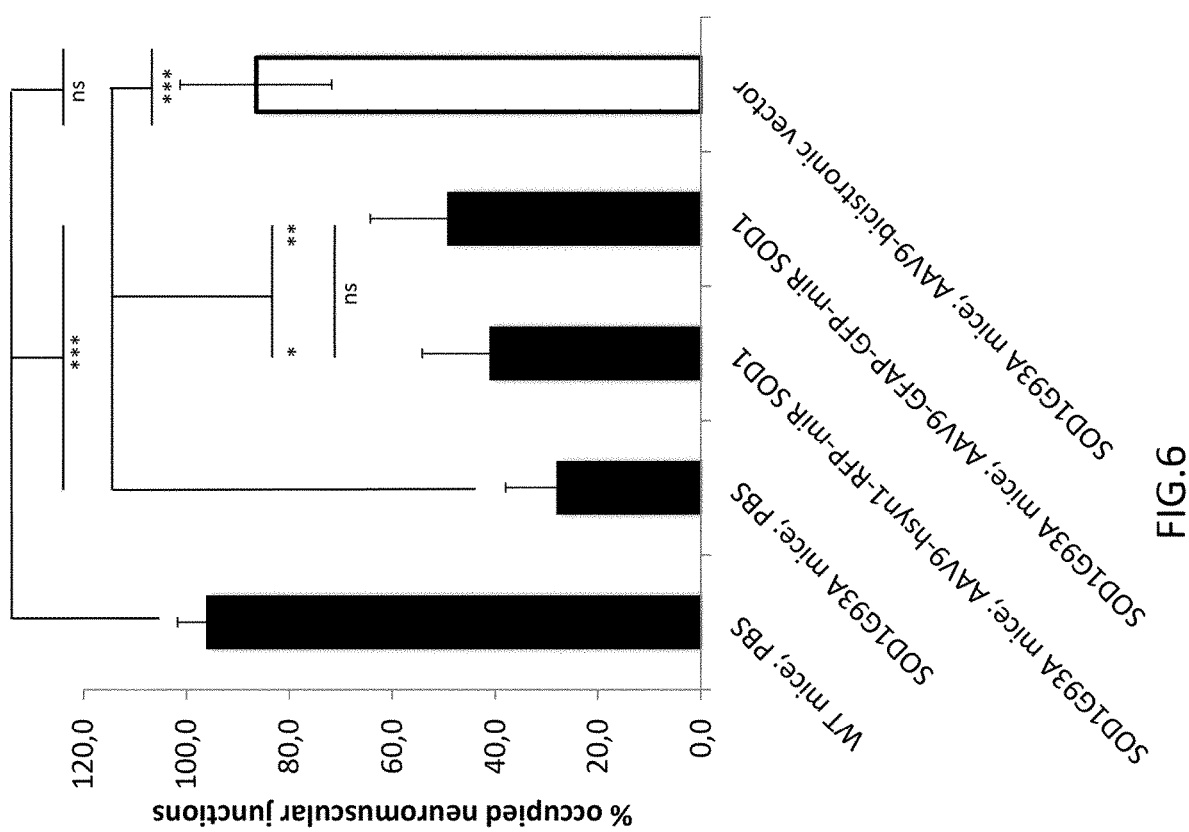
FIG. 6: Neuromuscular junction integrity expressed as percentage of bungarotoxin-positive motor end plates that are occupied by a SV2-positive motoneuron terminal. Innervation is fully preserved in the bicistronic group (white column), which is significantly different from the partial preservation in the other treated groups.

The FIGS. 5 and 6 confirm at a histological level that silencing SOD1 in both neurons and astrocytes using the bicistronic vector has a greater therapeutic outcome than SOD1 silencing in only one of the two cell types. Spinal cord sections were obtained from treated animals at end stage. Choline acetyltransferase (ChAT)-positive motoneurons were counted in the lumbar region of the spinal cord. Indeed, at the level of motoneuron survival (FIG. 5) the bicistronic vector shows a statistically significant increase in motoneuron survival when compared to vectors expressing miR SOD1 under the control of either the GFAP or the hsyn promoter alone.

Neuromuscular junction (NMJ) integrity (FIG. 6) has then been assessed. NMJ occupancy was evaluated on 20 µm muscle sections stained with an anti-SV-2 (Developmental Studies Hybridoma Bank, University of Iowa, Iowa City, Iowa) or VAChT antibody and tetramethylrhodamine α-bungarotoxin (Invitrogen). About 100 bungarotoxin-positive motor end plates were identified and checked for overlapping SV-2 or VAChT-positive motoneuron terminal using an Olympus AX70 microscope or Leica DM5500 microscope. The bicistronic vector (white column) shows a higher percentage of bungarotoxin-positive motor end plates that are occupied by a SV2-positive motoneuron terminal when compared to the vector with the vectors expressing miR SOD1 under the control of either the GFAP or the hsyn promoter alone.

The invention claimed is:

1. A bicistronic expression vector for silencing a gene in astrocytes and neurons comprising two expression cassettes,
   wherein a first cassette comprises "astrocyte specific promoter-posttranscriptional regulatory element-the first silencer sequence-polyA tail" and
   a second cassette comprises "neuron specific promoter-posttranscriptional regulatory element-the second silencer sequence-polyA tail";
   wherein, when injected into a subject, the bicistronic expression vector is able to target both the astrocytes and neurons brain cell populations with one injection.

2. The bicistronic vector according to claim 1, wherein said first and second silencer sequences are both SOD1 silencer sequences.

3. The bicistronic vector according to claim 2, wherein said SOD1 silencer sequences are independently selected from the group comprising RNA sequences that can be transcribed from DNA to interfere with SOD1 expression, including small hairpin RNA (shRNA) against SOD1, micro RNA (miRNA) against SOD1, antisense RNA sequences against SOD1 and guide RNA sequences for CRISPR/Cas9 mediated targeting of the SOD1 gene.

4. The bicistronic vector according to claim 1, wherein said first and second silencer sequences are both a miRNA designed to suppress SOD1 expression (miR SOD1).

5. A bicistronic expression vector for silencing a gene in astrocytes and neurons comprising two expression cassettes,
   wherein a first cassette comprises "astrocyte specific promoter-posttranscriptional regulatory element-the first silencer sequence-polyA tail" and a second cassette comprises "neuron specific promoter-posttranscriptional regulatory element-the second silencer sequence-polyA tail";
   wherein said first and second silencer sequences are both a miRNA designed to suppress SOD1 expression (miR SOD1); and,
   wherein said miR SOD1 targets the coding sequence of human SOD1 (NM 000454), nt 209-229 (miR SOD1) (SEQ ID No. 2).

6. A bicistronic expression vector for silencing a gene in astrocytes and neurons comprising two expression cassettes, wherein a first cassette comprises "astrocyte specific promoter-posttranscriptional regulatory element-the first silencer sequence-polyA tail" and a second cassette comprises "neuron specific promoter-posttranscriptional regulatory element-the second silencer sequence-polyA tail";
   wherein said first and second silencer sequences are both a miRNA designed to suppress SOD1 expression (miR SOD1); and,
   wherein said miRNA sequence comprises a 6 or 7 nucleotides-long "seed" sequence as shown in SEQ ID No. 2 which is fully homologous to the human SOD1 mRNA transcript (NM_000454).

7. A bicistronic expression vector for silencing a gene in astrocytes and neurons comprising two expression cassettes,
   wherein a first cassette comprises "astrocyte specific promoter-posttranscriptional regulatory element-the first silencer sequence-polyA tail" and a second cassette comprises "neuron specific promoter-posttranscriptional regulatory element-the second silencer sequence-polyA tail";
   wherein said first and second silencer sequences are both a miRNA designed to suppress SOD1 expression (miR SOD1); and,
   wherein said miR SOD1 mature sequence has at least 50%, 60%, 80%, still more preferably 90% sequence identity with the corresponding coding sequence set forth in SEQ ID No 1: 5'-ATT ACT TTC CTT CTG CTC GAA-3' (SEQ ID, No 1).

8. The bicistronic vector according to claim 7, wherein said miR SOD1 mature sequence corresponds to the coding sequence: 5'-ATT ACT TTC CTT CTG CTC GAA-3' (SEQ ID. No. 1).

9. The bicistronic vector according to claim 1, wherein said astrocyte specific promoter is selected from the group comprising the GFAP promoter, the glutamine synthase promoter, and minimal GFAP promoter gfaABC$_1$D.

10. The bicistronic vector according to claim 1, wherein said neuron specific promoter is selected from the group comprising synapsin, cmv, platelet-derived growth factor B-chain (PDGF-β), the methyl-CpG binding protein 2 (MeCP2), and human synapsin I promoter hSyn1.

11. The bicistronic vector according to claim 1, wherein said vector is an Adeno-Associated Viral (AAV) vector.

12. The bicistronic vector according to claim 11, wherein said AAV vector is of a serotype compatible with widespread transgene delivery to astrocytes and motoneurons, including serotype 9 or of serotype 6.

13. A method of treating of motoneuron diseases, including amyotrophic lateral sclerosis (ALS), comprising injecting a bicistronic expression vector according to claim 1 into a subject in need thereof.

14. A pharmaceutical composition comprising a bicistronic AAV vector comprising two expression cassettes comprising a first and a second gene silencer sequence,
   wherein the expression of said first silencer sequence within astrocytes is regulated by an astrocyte-specific promoter and the expression of said second silencer sequence within neurons is regulated by a neuron-specific promoter and a pharmaceutically acceptable carrier and,
   wherein, when the pharmaceutical composition is injected into a subject, the bicistronic expression vector is able to target both the astrocytes and neurons brain cell populations with one injection.

15. The pharmaceutical composition according to claim 14 for use in the treatment of motoneuron diseases, including amyotrophic lateral sclerosis (ALS).

16. A method of using an AAV vector-based biological delivery and expression system according to claim 1 for expressing a first and a second silencer sequence in astrocytes and motoneurons.

* * * * *